United States Patent

Chuang et al.

[11] Patent Number: 5,972,329
[45] Date of Patent: Oct. 26, 1999

[54] FIXATIVE POLYMERS

[75] Inventors: Jui-Chang Chuang, Wayne; Jenn S. Shih, Paramus; Russell B. Biss, Wayne, all of N.J.

[73] Assignee: ISP Investments Inc., Wilmington, Del.

[21] Appl. No.: 09/034,574

[22] Filed: Mar. 4, 1998

Related U.S. Application Data

[63] Continuation-in-part of application No. 08/857,954, May 16, 1997, Pat. No. 5,830,439.

[51] Int. Cl.⁶ .................. C08F 4/38; C08F 4/04; C08F 6/10; C08F 218/08
[52] U.S. Cl. ............ 424/78.31; 426/73; 426/218.1; 426/219.5; 426/228; 426/330
[58] Field of Search .................. 424/45, 78.31, 424/78.35; 426/73, 218.1, 219.5, 228, 330

[56] References Cited

U.S. PATENT DOCUMENTS 4,129,703   12/1978   Kamath et al. .
5,275,811   1/1994   Chuang et al. .

Primary Examiner—Edward J. Webman
Attorney, Agent, or Firm—Walter Katz; William J. Davis; Marilyn J. Maue

[57] ABSTRACT

An improved hydrocarbon tolerant, aerosol hair spray resin composition includes a fixative polymer which is a tetrapolymer consisting essentially of (1) vinyl acetate, (2) vinyl neodecanoate or vinyl neononanoate, (3) monoisobutyl maleate and (4) N-t-butyl acrylamide, N-t-octyl acrylamide, or isobornyl (meth)acrylate, in a molar ratio from 10:10:15:1 to 26:1:15:1, preferably in a molar ratio of 12.5:7.5:15:1, exhibits advantageous small spray particle size, short tack and drying times, and hydrolytic stability, which are the desired performance characteristics on hair.

7 Claims, No Drawings

5,972,329

FIXATIVE POLYMERS

CROSS-REFERENCE TO RELATED PATENT APPLICATION

This application is a continuation-in-part of copending U.S. patent application, Ser. No. 08/857,954, filed May 16, 1997, new U.S. Pat. No. 5,830,439, and assigned to the same assignee as herein.

BACKGROUND OF THE INVENTION

1. Field of the Invention

This invention relates to hair spray resin compositions, and, more particularly, to fixative polymers for use in hydrocarbon tolerant aerosol formulations which exhibit advantageous small spray particle size, short tack and drying time, and hydrolytic stability, which are advantageous performance characteristics on hair.

2. Description of the Prior Art

Effective hair spray formulations and film-forming resins must meet a rigid set of requirements. Specifically, the film-forming resins should remain non-tacky in a humid environment but be easily removed using soap solutions such as shampoos. The film should have high hair cohesivity and possess sufficient strength and elasticity so as to avoid dusting or flaking when the hair is subjected to combing or brushing tresses, and remain clear, transparent and glossy on aging. The film-forming resin should have a viscosity range which permits spraying without nozzle clogging, and should show little or no tendency to interact with perfumes or other optional components typically utilized in a hair spray formulation. The resin should also be readily soluble in various solvents while exhibiting good compatibility with conventional propellants such as hydrocarbons, dimethyl ether, or mixtures thereof.

Many polymeric systems have been developed in an attempt to meet these stringent requirements. Among these are polyvinylpyrrolidone and copolymers of N-vinylpyrrolidone with vinyl acetate. However, these copolymers do not exhibit the desired degree of holding under high humidity conditions. Methyl vinyl ether/maleic acid half ester copolymers also have been used in hair sprays but these must be of a relatively high molecular weight to achieve adequate holding. Vinyl acetate polymers having 15 to 35 percent of their acetate groups converted to hydroxyl groups have been proposed for increased solubility in carbon dioxide propellant systems. However such increased solubility is achieved at the cost of lower holding power. While each of the above resins meets at least some of the above cited requirements, none exhibit all of these characteristics to a satisfactory degree.

Chuang, in U.S. Pat. Nos. 4,689,379; 4,961,921; 5,196,495 and 5,275,811; described improved hair fixative resins which were terpolymer resins of random or alternating structure having (1) a vinyl ester, (2) a water-insoluble or water-miscible alkyl maleate half-ester and (3) an acrylate or methacrylate ester of a saturated hydroxylated bicyclic hydrocarbon, or an N-substituted acrylamide. The resin was prepared in the form of beads or microspheres by suspension polymerization to provide a suitably high molecular weight for improved hair holding under humid conditions.

Other related hair spray compositions in this field include U.S. Pat. Nos. 3,145,147; 4,223,009; 4,842,852; 4,859,455; 4,923,695 and 4,933,170.

Accordingly, it is an object of the present invention to provide a hydrolytically stable hydrocarbon tolerant hair spray resin composition which can develop fine spray patterns, and which exhibits prolonged curl retention under humid conditions, short tack and drying times, good holding power, ease of removability and resistance to polymer build-up.

These and other objects and features of the invention will be made apparent from the following more particular description thereof.

SUMMARY OF THE INVENTION

What is described herein is a fixative polymer for use in hydrolytically stable, hydrocarbon tolerant hair spray resin composition consisting essentially of a tetrapolymer which comprises (1) vinyl acetate, (2) vinyl neononanoate or vinyl neodecanoate, (3) monoisobutyl maleate and (4) N-t-butyl acrylamide, N-t-octyl acrylamide, or isobornyl (meth) acrylate, in a molar ratio from 10:10:15:1 to 26:1:15:1, preferably in a molar ratio of 12.5:7.5:15:1, respectively, which is capable of forming dispersed spray particles of advantageously small particle size, and which demonstrates short tack and drying times and high humidity curl retention on hair.

DETAILED DESCRIPTION OF THE INVENTION

In the preferred form of the invention, there is described herein a hydrocarbon tolerant, aerosol hair spray composition which includes a fixative polymer which is a tetrapolymer resin consisting essentially of, by weight, (a) about 15–45% vinyl acetate (VA), (b) about 5–40% vinyl neononanoate (VNN) or vinyl neodecanoate (VND), (c) about 30–60% mono-isobutyl maleate (MIBM), and (d) about 1–10% isobornyl acrylate (IBA), N-t-butylacrylamide (BAA) or N-t-octylacrylamide (OAA). A preferred tetrapolymer resin composition consisting essentially of (a) 20% VA, (b) 28% VNN or VND, (c) 48% MIBM and (d) 4% IBA, BAA or OAA.

The presence of the VNN or VND monomer in the tetrapolymer resin of the invention increases the hydrophobic character of the polymer and enhances its hydrocarbon tolerance to ≧50% of an aerosol composition containing the tetrapolymer. In combination with components (a), (c) and (d), the presence of (b) provides an aerosol spray formulation which exhibits smaller spray particle size, shorter tack time and shorter drying time, compared to formulations containing commercially available hair spray resins such as Amphomer® resin from National Starch and Chemical Corporation. These differences are observed herein because the VNN or VND component in the tetrapolymer of the invention imparts a 20° C. increase in its glass transition as compared to the same resin without VNN or VND present. Furthermore, the resin provides an enhanced stiff feel on hair, and improved curl retention, shine, comb drag, comb residue and manageability, which characteristics are desirable performance properties for the consumer.

The tetrapolymer herein can be prepared by suspension polymerization in water, or by solution polymerization in acetone, followed by acetone-ethanol exchange. Suspension polymerization is preferred because the resin is obtained in the form of dry beads or microspheres which are easy to handle. The tetrapolymer resin obtained by either process, however, has a high molecular weight, which provides enhanced hair holding under humid conditions.

When synthesized by the suspension polymerization process, the microspheres of the tetrapolymer resin generally have an average diameter of between about 0.05 and about 2.5 mm. The polymer products produced by either suspension or solution polymerization possess a relative viscosity (RV), measured at 1 g tetrapolymer per 100 ml of an ethanol solution at 25° C., in the range of about 1.2–2.0, preferably about 1.25–1.50.

In general suspension polymerization involves charging the monomers individually or premixed in the above proportions, either at start or over time, to a 0.1 to 2.0% by weight aqueous suspension medium, preferably a 0.25 to 1.0 weight % solution, of a carboxylated polyelectrolyte, preferably methyl vinyl ether-maleic acid copolymer (GANTREZ® S-95 or S-97 produced by International Specialty Products, Inc.). Polymerization is carried out in the presence of a free radical initiator, or a mixture of free radical initiators, under conditions of agitation at a temperature of between about 40° and about 90° C., preferably between about 55° and about 75° C. The initiator(s) can be added to the monomer mixture before or after the monomers have been charged into the suspension medium. The reaction is carried out in an inert atmosphere which can be maintained by purging with nitrogen to eliminate oxygen.

The polymerization reaction is carried out under constant agitation over a period of from about 4 to about 12 hours; typically 6 to 8 hours is sufficient to complete the reaction and form a bead-like tetrapolymer product. The beads are then separated from the suspension medium, washed with water, and dried. The supernatant liquid which is separated from the product can be recycled to the reaction zone if desired as a make-up suspension media in which any unreacted monomer in the supernatant liquid can be converted, thus providing a highly efficient, pollution-free process.

The concentration of total monomers in the suspension medium can vary from about 10 to 50 wt. %. However, concentrations of between about 20 and about 40 wt. % are recommended as being the most economical.

Generally, between about 0.05 and about 5.0 wt. % initiator, based on total monomers of the tetrapolymer, can be employed in the polymerization reaction although, in most instances, between about 0.5 and about 3.0 wt. % initiator is sufficient to promote the reaction.

The free radical initiators employed in the present reaction are typically low temperature initiators having a half-life of 10 hours at temperatures between about 45° and 65° C., although any of the free radical initiators which are effective at temperatures between about 30° C. and about 80° C. are suitably employed herein. Typical of such initiators include peroxyesters such as t-butyl peroxypivalate (Lupersol® 11), t-amyl peroxypivalate (Lupersol® 554), t-amyl peroctoate (Lupersol® 575), peroxydicarbonates such as di-(n-propyl) peroxydicarbonate (Lupersol® 221), di-(sec-butyl) peroxydicarbonate (Lupersol® 225) and di-(2-ethylhexyl) peroxydicarbonate (Lupersol® 223) all supplied by Elf Atochem N.A. Also, azo initiators such as 2,2'-azobis(2,4-dimethylvaleronitrile) (VAZO® 52) and 2,2'-azobis(2,4-dimethyl-4-methoxyvaleronitrile) (VAZO® 33W), both supplied by DuPont, are suitable.

Preferably, a combination of a low temperature initiator such as Lupersol® 223 and a longer half-life second initiator such as Lupersol® 11, Lupersol® 554, 2,2'-azobisisobutyronitrile (VAZO® 64) or 2,2'-azobisisovaleronitrile (VAZO® 67) is employed. The low temperature initiator starts the polymerization at a temperature of about 55–65° C. and the longer half-life initiator completes the polymerization at a higher temperature of 70–90° C.

Another feature of the suspension polymerization process of the present invention is the use of azeotropic distillation to remove residual monomers and other volatile substances from the reaction product. This step is carried out by adding a suitable amount of water to the product of polymerization and distilling at 100° C.

The tetrapolymer resins can also be produced by a solution polymerization process. In this method monomers are added to an organic solvent such as acetone, along with an initiator, as previously described. The monomers may be premixed, or added individually to the solvent. The monomers should be in a concentration of about 50–70%. If the monomer mixture becomes too thick during polymerization, additional solvent can be added. The initiator causes the monomers to polymerize and form the tetrapolymer. Preferably, polymerization occurs during agitation in a reaction zone maintained at a temperature between about 30° C. and 90° C., until the reaction is complete. After completion, the tetrapolymer is recovered from the organic solvent by a solvent exchange process, i.e. exchanging the organic solvent for an alcohol such as ethanol. This may be done by distillation, solvent extraction or other means. The organic solvent may be reused after recovery. By varying the solvent to monomer ratio, the relative viscosity (RV) of the product can be adjusted. For example, a 50% monomer concentration may yield a RV of 1.3, a 70% concentration, a RV of 1.5, and a 25% concentration, a RV of 1.05. The solution polymerization process is somewhat longer than the suspension process, taking typically from 12–16 hours.

The present tetrapolymeric resins are employed as the active ingredients in hair spray formulations employed for aerosol and pump sprays as well as for styling gels and styling mousse. The resins can also be used to augment existing hair spray formulations to improve solubility, hair holding and propellant compatibility. When used as the sole active hair holding agent in the formulation, the present resins are employed in concentrations between about 1.0% and about 6%, preferably between about 2.0% and about 5.0% for aerosol and between about 3 and about 5% for pump sprays. Generally the resin is about 50–100% neutralized.

In preparing the hair treatment formulations, the tetrapolymer resin is usually dissolved in an inert carrier, such as a lower alcohol, e.g. ethanol, an aqueous ethanol solution, isopropanol or the like. For aerosol sprays, the formulations may also include a conventional propellant such as, for example, a 20/80 blend of propane/isobutane (Propellant A-46), dimethyl ether, difluoroethane, nitrogen, nitrogen oxide, carbon dioxide, or mixtures thereof.

The formulations are charged into a canister and the propellant pressurized into the canister to provide a spray operated through a pressure release nozzle. The present resins have a long shelf life and avoid nozzle clogging or canister corrosion when employed in the above concentrations.

Having thus generally described the invention, reference is now had to the following examples which provide specific and preferred embodiments but which are not to be construed as limiting the scope of the invention as more broadly described above and in the appended claims. All parts given are by weight unless otherwise indicated.

EXAMPLE 1

(Control)

This control example describes suspension polymerization of a vinyl acetate/mono-n-butyl maleate/ isobornyl acrylate (38/57/5) terpolymer, as taught in Example 7 of U.S. Pat. No. 4,689,379. The molar ratio of vinyl acetate, mono-n-butyl maleate and isobornyl acrylate was 1:0.75:0.05. All monomers and polymerization initiator were precharged before heating to the polymerization temperature.

Into a 1-liter, 4-necked resin kettle equipped with a pitch blade agitator, a thermocouple, a reflux condenser and nitrogen inlet tube was charged 210.0 g of a 0.5% aqueous solution of GANTREZ® S-97. The monomer pre-mix was then added:

- 68.80 g of vinyl acetate (0.80 mole),
- 103.20 g of mono-n-butyl maleate (0.60 mole),
- 8.32 g of isobornyl acrylate (0.04 mole) and
- 3.60 g of di-(2-ethylhexyl)peroxydicarbonate (Lupersol® 223M75, 75% active) initiator.

The reactor contents were agitated at 275 rpm under nitrogen sparging (2 SCFH) for 15 minutes at room temperature. Nitrogen tube was kept above the liquid level during the reaction to avoid composition drift. The reaction mixture was then heated in a water bath to 62° C. over 15 minutes while maintaining agitation and nitrogen sparging. The reactants were held at 62° C. for 3 hours and at 68° C. for 4 hours during which the resin in microspheric form was formed.

The reaction product was cooled to 25° C. in 30 minutes and the supernate decanted. The remaining polymer beads, having an average 0.6–1.2 mm in diameter, were washed with distilled water, filtered on a Buchner funnel with vacuum suction for half hour. The polymer wet cake containing 16% water was tray dried at ambient temperature for 3 hours and then in a 70° C. forced air oven for 5 hours. After cooling to ambient temperature, the resin in bead form, referred as Polymer 1, was recovered in 93.5% yield, a relative viscosity of 1.549 (1% resin solution in absolute ethanol, K-value of 45.4), an acid number of 196 mg KOH/g and a glass transition temperature ($T_g$) of 83° C.

EXAMPLE 2

(Control)

This example describes suspension polymerization of a vinyl acetate/mono-n-butyl maleate/N-t-butylacrylamide (35/59/6) terpolymer, as taught in Example 7 of U.S. Pat. No. 5,196,495. The molar ratio of vinyl acetate, mono-n-butyl maleate and N-t-butylacrylamide is 1:0.75:0.10. All monomers and polymerization initiator were precharged before heating to the polymerization temperature.

Into a 1-liter, 4-necked resin kettle equipped with a pitch blade agitator, a thermocouple, a reflux condenser and nitrogen inlet tube was charged 425.0 g of a 0.25% GANTREZ® S-97 aqueous solution. The following monomer pre-mix was then added:

- 68.80 g of vinyl acetate (0.80 mole),
- 103.20 g of mono-n-butyl maleate (0.60 mole),
- 10.16 g of N-t-butylacrylamide (0.08 mole) and
- 2.73 g of di-(2-ethylhexyl)peroxydicarbonate (Lupersol 223M75, 75% active) initiator.

The reactor contents were agitated at 300 rpm under nitrogen sparging (2 SCFH) for 15 minutes at room temperature. Nitrogen tube was kept above the liquid level during the reaction to avoid composition drift. The reaction mixture was then heated in a water bath to 62° C. over 15 minutes while maintaining agitation and nitrogen sparging. The reactants were held at 62° C. for 3 hours and at 68° C. for 3 hours during which the resin in microspheric form was formed.

The reaction product was cooled to 25° C. in 30 minutes and the supernate decanted. The remaining polymer beads, having an average 0.8–1.5 mm in diameter, were washed with distilled water, filtered on a Buchner funnel with vacuum suction for half hour. The polymer wet cake containing 15% water was tray dried at ambient temperature for 3 hours and then in a 70° C. forced air oven for 5 hours. After cooling to ambient temperature, the resin in bead form, referred as Polymer 2, was recovered in 88.8% yield, a relative viscosity of 1.611 (1% resin solution in absolute ethanol, K-value of 47.7), an acid number of 203 mg KOH/g and a glass transition temperature ($T_g$) of 88° C.

EXAMPLE 3

This example illustrates the suspension polymerization of vinyl acetate/vinyl neononanoate/mono-iso-butyl maleate/isobornyl acrylate (21/26/49/4) tetrapolymer of this invention. The polymer achieves high compatibility with hydrocarbon propellant by replacing vinyl acetate with a mixture of vinyl acetate and a long-chain, branched vinyl ester. All monomers and polymerization initiator were pre-mixed and charged into the reactor over time at the polymerization temperature. Any residual monomer was removed by azeotropic distillation at the end of polymerization.

Into a 1-liter, 4-necked resin kettle equipped with a pitch blade agitator, a thermocouple, a reflux condenser and nitrogen inlet tube was charged 490.0 g of a 0.25% GANTREZ® S-97 aqueous solution. The reactor contents were agitated at 300 rpm under nitrogen sparging (2 SCFH) and heated in a water bath to 55° C. over 30 minutes. The following monomer pre-mix along with the polymerization initiator was prepared and subsurface fed into the reactor at 55° C. over one hour:

- 43.00 g of vinyl acetate (0.50 mole),
- 55.20 g of vinyl neononanoate (0.30 mole)
- 103.20 g of mono-iso-butyl maleate (0.60 mole),
- 8.32 g of isobornyl acrylate (0.04 mole),
- 2.10 g of di-(2-ethylhexyl)peroxydicarbonate (Lupersol® 223M75, 75% active) initiator.

During the reaction period, nitrogen sparging tube was kept above the liquid level to avoid composition drift. The reactants were held at 55–57° C. for 3 hours and at 68–70° C. for 3 hours during which the resin in microspheric form was formed. After adding 300 ml of distilled water, the reactor contents were then raised to 100° C. Residual monomers were azeotropically distilled out in one hour and about 300 ml of distillate were collected.

The reaction product was cooled to 25° C. in 30 minutes and the supernate decanted. The remaining polymer beads were washed with distilled water, filtered on a Buchner funnel with vacuum suction for half hour. The polymer wet cake containing 12% water was tray dried in a 90° C. forced air oven for 3 hours. After cooling to ambient temperature, the resin in bead form having an average 0.4–1.0 mm in diameter, referred as Polymer 3, was recovered in 97.7% yield, a relative viscosity of 1.568 (1% resin solution in absolute ethanol, K-value of 46.1), an acid number of 159 mg KOH/g and a glass transition temperature ($T_g$) of 110° C.

EXAMPLE 4

This example illustrates the suspension polymerization vinyl acetate/vinyl neononanoate/mono-iso-butyl maleate/isobornyl acrylate (16/33/47/4) tetrapolymer of this invention. The preparation procedure was identical to Example 3 except the monomer composition was altered. All monomers and the polymerization initiator were pre-mixed and were charged into polymerization reactor over time at the polymerization temperature. Any un-reactive residual monomers were removed by azeotropic distillation at the end of polymerization.

Into a 1-liter, 4-necked resin kettle equipped with a pitch blade agitator, a thermocouple, a reflux condenser and nitrogen inlet tube was charged 300.0 g of 0.5% GANTREZ® S-97 aqueous solution. The reactor contents were agitated at 300 rpm under nitrogen sparging (2 SCFH) and heated in a water bath to 55° C. over 30 minutes. The following monomer pre-mix along with polymerization initiator was prepared and subsurface fed into the reactor at 55° C. over one hour:

34.40 g of vinyl acetate (0.4 mole), 73.60 g of vinyl neononanoate (0.4 mole)

103.20 g of mono-iso-butyl maleate (0.6 mole), 8.82 g of isobornyl acrylate and (0.04 mole), 4.40 g of di-(2-ethylhexyl)peroxydicarbonate (Lupersol® 223M75, 75% active) initiator.

During the reaction period, nitrogen sparging tube was kept above the liquid level to avoid composition drift. The reactants were held at 55–57° C. for 5 hours and at 74–76° C. for 2 hours during which the resin in microspheric form was formed. After adding 300 ml of distilled water, the reactor contents were then raised to 100° C. Residual monomers were azeotropically distilled out in one hour and about 300 ml of distillate were collected.

The reaction product was cooled to 25° C. in 30 minutes and the supernate decanted. The remaining polymer beads were washed with distilled water, filtered on a Buchner funnel with vacuum suction for half hour. The polymer wet cake containing 11% water was tray dried in a 60° C. forced air oven for 3 hours and then at 95° C. for 2 hours. After cooling to ambient temperature, the resin in bead form having an average 0.4–1.0 mm in diameter, referred as Polymer 4, was recovered in 96.0% yield, a relative viscosity of 1.381 (1% resin solution in absolute ethanol, K-value of 38.0), an acid number of 150 mg KOH/g and a glass transition temperature ($T_g$) of 118° C.

EXAMPLES 5–15

In Examples 5–15 the preparation procedure identical to that described in Example 3 was repeated to synthesize the corresponding Polymers 5–15 except the following modifications on monomer composition, polymerization initiators, suspending agent concentration and/or reaction conditions.

Examples 5–12 were modified by replacing vinyl neononanoate with vinyl neodecanoate monomer and di-(2-ethylhexyl)peroxydicarbonate was replaced by a mixture of a peroxydicarbonate and a peroxyester. Satisfactory results were also obtained when a VAZO® initiator was used in place of the peroxyester. The weight ratios of the monomer compositions, polymerization initiators, suspending agent concentration and/or polymerization temperature were altered, as shown in Table 1. Also in Example 7–9, the peroxyester initiator t-butyl peroxypivalate (Lupersol® 11, 75% active) was replaced by t-amyl peroxypivalate (Lupersol® 554, 75% active). In Example 11, mono-iso-butyl maleate was replaced by mono-n-butyl maleate and in Example 12, isobornyl acrylate was replaced by isobornyl methacrylate.

In Examples 13–15 the preparation procedure identical to that described in Example 3 was repeated to synthesize the corresponding Polymers 13–15. In Example 13, isobornyl acrylate was replaced by N-t-butylacrylamide and the monomer composition was modified. In Example 14, isobornyl acrylate was replaced by N-t-octylacrylamide and the monomer composition was also modified. In Example 15, vinyl neononanoate was replaced by vinyl neodecanoate and isobornyl acrylate was replaced by N-t-butylacrylamide.

Polymers 3–15 were analyzed and characterized as shown in Table 1.

TABLE 1

| Polymer | 3 | 4 | 5 | 6 | 7 | 8 | 9 | 10 | 11 | 12 | 13 | 14 | 15 |
|---|---|---|---|---|---|---|---|---|---|---|---|---|---|
| Vinyl Acetate | 21.0 | 16.0 | 24.0 | 20.0 | 20.0 | 15.0 | 26.0 | 26.0 | 20.0 | 20.0 | 16.0 | 20.0 | 20.0 |
| Vinyl Neononanoate | 26.0 | 33.0 | | | | | | | | | 33.0 | 25.0 | |
| Vinyl Neodecanoate | | | 24.0 | 28.0 | 28.0 | 33.0 | 20.0 | 30.0 | 28.0 | 28.0 | | | 28.0 |
| Mono-n-butyl Maleate | | | | | | | | | 48.0 | | | | |
| Mono-iso-butyl Maleate | 49.0 | 47.0 | 48.0 | 48.0 | 48.0 | 48.0 | 50.0 | 40.0 | | 48.0 | 46.0 | 48.0 | 48.0 |
| Isobornyl Acrylate | 4.0 | 4.0 | 4.0 | 4.0 | 4.0 | 4.0 | 4.0 | 4.0 | 4.0 | | | | |
| Isobornyl Methacrylate | | | | | | | | | | 4.0 | | | |
| N-t-Butylacrylamide | | | | | | | | | | | 5.0 | | 4.0 |
| N-t-Octylacrylamide | | | | | | | | | | | | 7.0 | |
| D-(2-ethylhexyl) peroxydicarbonate | 1.0 | 2.0 | 2.0 | 2.0 | 2.0 | 2.0 | 2.0 | 2.0 | 2.0 | 2.0 | 1.5 | 1.0 | 2.0 |
| t-Butyl Peroxypivalate | | | 1.0 | 1.0 | | | | 1.0 | 1.0 | 1.0 | | | 1.0 |
| t-Amyl Peroxypivalate | | | | | 1.0 | 1.0 | 1.0 | | | | | | |
| Gantrez S-97 in water, wt. % | 0.5 | 0.5 | 0.5 | 0.5 | 0.25 | 0.5 | 0.5 | 0.5 | 0.5 | 0.5 | 0.5 | 0.5 | 0.5 |
| Polymerization Temperature, ° C. | 55/68 | 55/75 | 55/75 | 55/75 | 55/68 | 55/68 | 55/68 | 55/75 | 55/75 | 55/75 | 62/68 | 60/68 | 55/75 |
| % Yield | 93.9 | 96.0 | 95.3 | 95.0 | 95.5 | 96.1 | 94.9 | 95.3 | 94.8 | 95.5 | 94.8 | 95.0 | 96.0 |
| Polymer Characteristics | | | | | | | | | | | | | |
| Relative Viscosity, 1% in ethanol | 1.568 | 1.381 | 1.471 | 1.506 | 1.522 | 1.475 | 1.523 | 1.482 | 1.508 | 1.425 | 1.399 | 1.633 | 1.527 |
| K-Value | 46.1 | 38.0 | 42.2 | 43.7 | 44.3 | 42.3 | 44.4 | 42.6 | 43.7 | 40.1 | 38.9 | 48.5 | 44.5 |
| Acid Number, mg KOH/g | 159 | 150 | 159 | 155 | 158 | 152 | 167 | 131 | 156 | 149 | 143 | 155 | 156 |
| Glass Transition Temperature, $T_g$, ° C. | 110 | 118 | 99 | 102 | 102 | 104 | 103 | 101 | 93 | 106 | 123 | 111 | 109 |

EXAMPLE 16

This example illustrates the excellent solution properties of the hair spray resins of this invention, as compared to commercial hair spray resins such as Resyne® 28–2930 and Amphomer® 28–4910 from the National Starch and Chemical Corporation and to the art of U.S. Pats. Nos. 4,689,379 and 5,196,495.

The hair spray resins of Examples 1–15 and commercial hair spray resins such as Resyn® 28-2930 and Amphomer® 28-4910 were evaluated for its solubility in ethanol and in ethanol/n-heptane mixture without the presence of a neutralizing agent. In these tests, 5.0 g of each polymer were dissolved in (1) 95.0 g of anhydrous ethanol (SDA 40B grade), (2) 65.0 g of anhydrous ethanol and 30 g of n-heptane and (3) 45.0 g of anhydrous ethanol and 50 g of n-heptane, respectively, under agitation at 25° C. and the clarity of the solution was recorded. Testing results are rated as clear, soluble but hazy or insoluble and are shown in Table 2. In addition, all of the polymers of this invention (Polymers 3–15) at 5% solids in the ethanol/n-heptane (45/50) mixture remained clear at a temperature below –18° C. (0° F.).

TABLE 2

| Polymer | 5% Solubility in Ethanol | 5% Solubility in Ethanol/Heptane (65/30) | 5% Solubility in Ethanol/Heptane (45/50) |
|---|---|---|---|
| Resyn ® 28-2930* (control) | slightly hazy** | hazy*** | hazy |
| Amphomer ® 28-4910* (control) | slightly hazy** | clear*** | hazy |
| 1 (control) | clear | clear | hazy |
| 2 (control) | clear | clear | hazy |
| 3 | clear | clear | clear |
| 4 | clear | clear | clear |
| 5 | clear | clear | clear |
| 6 | clear | clear | clear |
| 7 | clear | clear | clear |
| 8 | clear | clear | clear |
| 9 | clear | clear | clear |
| 10 | clear | clear | clear |
| 11 | clear | clear | clear |
| 12 | clear | clear | clear |
| 13 | clear | clear | clear |
| 14 | clear | clear | clear |
| 15 | clear | clear | clear |

*Resyn ® 28-2930 is a vinyl acetate/crotonic acid/vinyl neodecanoate terpolymer and Amphomer ® 28-4910 is an N-t-octylacrylamide/methyl methacrylate/Acrylic acid/hydroxypropyl methacrylate/t-butlaminoethyl methacrylate copolymer.
**Both 5% of Resyn ® 28-2930 and Amphomer ® 28-4910 in anhydrous ethanol require 90% neutralization of carboxyl functionality with 2-amino-2-methyl-1-propanol (AMP) to obtain a clear solution.
***Clarity of 5 parts of hair spray resin (90% neutralized with AMP) in a mixture of 65 parts of anhydrous ethanol and 30 parts of n-heptane: Resyn ® 28-2930, hazy and Amphomer ® 28-4910, clear.

When n-heptane was replaced by propellant A-46 (a 20/80 propane/isobutane blend) in a separate test, each of Polymers 3–15 at 5% solids in the ethanol/propellant (45/50) was clear at –20° F. (–29° C.). Thus, n-heptane was an ideal substitute for evaluating the compatibility of resin in hydrocarbon propellant A-6. Testing results indicate that these polymers exhibit excellent compatibility with hydrocarbon propellant for aerosol hair spray applications.

EXAMPLE 17

This example provides a representative aerosol hair spray formulation using a typical $C_3$-$C_4$ hydrocarbon propellant. The resins were each dissolved in anhydrous ethanol, 100% neutralized with 2-amino-2-methyl-1-propanol (AMP) and charged to an aerosol spray can with hydrocarbon propellant A-46, as shown in Table 3.

TABLE 3

|  | Formulation A Wt., g | Formulation B Wt., g |
|---|---|---|
| Amphomer ® 28-4910 (control) | 5.0 | — |
| Hair Spray Resins of This Invention | — | 5.0 |
| Anhydrous Ethanol (SDA-40B) | 60.0 | 45.0 |
| Propellant A-46 | 35.0* | 50.0 |
| 2-Amino-2-methyl-1-propanol (AMP) | ** | ** |

*Amphomer ® 28-4910 is incompatible with propellant A-46 at a concentration greater than 35 wt. %.
**As required to 100% neutralization of carboxyl functionalities of the hair spray resin.

The aerosol hair sprays thus prepared were evaluated for their hair holding properties under high humidity conditions. The clean, dried tresses (2 g in weight, 10" in length) were each sprayed with the above formulations for 3 seconds at a distance of 2 inches, combed through twice, rolled on ⅝" roller and dried under a salon type dryer for one hour. These tresses were then unrolled on a humidity rack and placed in a 80° F., 90% relative humidity cabinet for 4 hours. The high humidity curl retention readings at 1.5 and 4 hours were recorded. The results of the relative curl retention at the 4-hour interval for Polymers 4, 6 and 13 are shown in Table 4 using Amphomer® 28-4910 as the control which is assigned as a value of 1.00.

TABLE 4

|  | Amphomer (Control) | Polymer 4 | Polymer 6 | Polymer 13 |
|---|---|---|---|---|
| Formulation |  |  |  |  |
| Hair Spray Resin, g | 5.0 | 5.0 | 5.0 | 5.0 |
| Anhydrous Ethanol (SDA-40B), g | 60.0 | 45.0 | 45.0 | 45.0 |
| Propellant A-46, g | 35.0* | 50.0 | 50.0 | 50.0 |
| 2-Amino-2-methyl-1-propanol (AMP) | ** | ** | ** | ** |
| Performance Characteristics on Hair |  |  |  |  |
| 4-Hour Relative Curl Retention | 1.00 | 1.04 | 1.07 | 1.10 |
| Stiffness on Hair | 8.2 | 9.1 | 9.2 | 8.7 |
| Removability from Hair (1 Application) | OK | OK | OK | OK |

*Amphomer 28-4910 is incompatible with propellant A-46 at a concentration greater than 35 wt. %.
**As required to 100% neutralization of carboxyl functionalities of the hair spray resin.

The results showed that both vinyl acetate/high vinyl ester/mono-alkyl maleate/isobornyl (meth)acrylate polymer and vinyl acetate/high vinyl ester/mono-alkyl maleate/N-t-alkylacrylamide polymer of this invention are superior in high humidity hair holding (4 hour intervals at 80° F. and 90% relative humidity) to a commercial hair spray resin such as Amphomer® 28-4910.

After completing the high humidity curl retention tests, a subjective test on the stiffness of the curl was evaluated on each polymer by compressing the curled tress between fingers by a panel of 5 trained persons, using scale 1–10, 10 being the very, very stiff and 1 being very, very soft (like natural hair). Results show that both vinyl acetate/high vinyl ester/mono-alkyl maleate/isobornyl (meth)acrylate polymer and vinyl acetate/high vinyl ester/mono-alkyl maleate/N-t-alkylacrylamide polymer of this invention exhibit superior stiffness on hair to a commercial hair spray resin such as Amphomer® 28-4910.

After testing for high humidity curl retention and stiffness, each polymer film was further evaluated for their removability from hair. Three drops of Prell® shampoo was applied to each hair tress. After working shampoo into a lather for 30 seconds, the hair tress was rinsed with warm tap water, the excess water was squeezed off and dried at 50° C. Each polymer of this invention was found to be removed easily in an aqueous shampoos or soap solutions, leaving no detectable residues.

EXAMPLE 18

This example demonstrates that aerosol hair spray formulations of the present invention exhibit the desired fine, disperse spray patterns (i.e., smaller droplet sizes) which has a lower tack and shorter drying time than a commercial hair spray resin such as Amphomer® 28-4910.

The aerosol hair spray compositions prepared from Example 17 in aerosol bottles fitted with a Precision valve. The particle size of the aerosol hair spray was determined by a Malvern Droplet and Particle Size Analyzer, Series 2600. Each aerosol resin bottle was set back 12 inches from the center of the laser beam and leveled and sprayed for 12 seconds and the particle size distribution was recorded. Tack time measures the rate of solvent evaporation which is required for drying a freshly applied hair spray from being sticky/tacky to touch. Drying time indicates time required to dry freshly applied hair spray completely. Each hair tress (about 3.5 g) was sprayed for a 2 second burst to front of tress from a distance of 8 inches and their tack time and drying time were determined by a panel of 5 trained persons. The results of the spray pattern, tack time and drying time as shown in Table 5, using Amphomer® 28-4910 as the control, showed the advantages of the composition of the invention over the control.

TABLE 5

| | Amphomer (Control) | Polymer 4 | Polymer 6 | Polymer 13 |
|---|---|---|---|---|
| Formulation | | | | |
| Hair Spray Resin, g | 5.0 | 5.0 | 5.0 | 5.0 |
| Anhydrous Ethanol (SDA-40B), g | 60.0 | 45.0 | 45.0 | 45.0 |
| Propellant A-46, g | 35.0* | 50.0 | 50.0 | 50.0 |
| 2-Amino-2-methyl-1-propanol (AMP) | ** | ** | ** | ** |
| Performance Characteristics of Hairsprays | | | | |
| Particle Size, microns | 69 | 52 | 47 | 60 |
| Tack Time, sec. | 42 | 17 | 39 | 25 |
| Drying Time, Sec. | 59 | 35 | 52 | 55 |
| Film Clarity (90% Relative Humidity) | Clear | Clear | Clear | Clear |

*Amphomer 28-4910 is incompatible with propellant A-46 at a concentration greater than 35 wt. %.
**As required to 100% neutralization of carboxyl functionalities of the hair spray resin.

While the invention has been described with particular reference to certain embodiments thereof, it will be understood that changes and modifications may be made which are within the skill of the art. Accordingly, it is intended to be bound only by the following claims, in which:

What is claimed is:

1. A suspension polymerization process of making the fixative tetrapolymer consisting essentially of (1) vinyl acetate, (2) vinyl neodecanoate or vinyl neononanoate, (3) monoisobutyl maleate and (4) N-t-butyl acrylamide, N-t-octyl acrylamide or isobornyl (meth)acrylate, in which said tetrapolymer has a molar ratio of 10:10:15:1 to 26:1:15:1, in the form of microspheres, which comprises polymerizing the monomer components in the presence of a dual initiator system which comprises a first low temperature initiator and a second, longer half-life, high temperature initiator.

2. A process according to claim 1 wherein the first initiator starts the polymerization at about 55–65° C. and the second initiat or completes the polymerization at about 65–90° C.

3. A process according to claim 1 wherein azeotropic distillation is used to remove residual monomers and other volatile substances from the reaction product.

4. A process according to claim 1 in which both initiators are present in the reaction mixture before polymerization of said monomers.

5. A process according to claim 1 in which said microspheres are beads having an average diameter of about 0.05 to 2.5 mm.

6. A process according to claim 1 in which the concentration of total monomers in the suspension medium is about 10 to 50 wt. %.

7. A process according to claim 1 in which about 0.05 to 5.0 wt. % of initiators, based on total monomers, is used in the polymerization.

* * * * *